United States Patent [19]

Bringhurst et al.

[11] Patent Number: Plant 5,266

[45] Date of Patent: Jul. 31, 1984

[54] STRAWBERRY PLANT 'SELVA'

[75] Inventors: Royce S. Bringhurst, Davis; Victor Voth, Santa Ana, both of Calif.

[73] Assignee: The Regents of the University of California, Berkeley, Calif.

[21] Appl. No.: 452,696

[22] Filed: Dec. 23, 1982

[51] Int. Cl.[3] ..... A01H 5/03

[52] U.S. Cl. ..... Plt./49

[58] Field of Search ..... Plt./49

*Primary Examiner*—Robert E. Bagwill

*Attorney, Agent, or Firm*—Townsend and Townsend

[57] ABSTRACT

A new and distinct variety of strawberry plant of the day-neutral type which is primarily characterized by its ability to fruit within three months after planting regardless of when planted or whether from fresh dug or cold storage plants. The variety is suitable for both summer and winter plantings, is self fertile and a good producer of runners in the nursery. The variety is further characterized by the tendency of only the mother and first daughter to flower and fruit strongly as opposed to other day-neutral varieties, such as 'Aptos', 'Brighton' and 'Hecker'. The fruit of the variety is firm and durable and much larger than that of 'Tioga'. It has a generally good flavor although moisture content is lower than varieties which are comparable. Its characteristics make it suitable for commercial uses as well as home gardening.

3 Drawing Figures

DESCRIPTION

This invention relates to a new and distinctive day-neutral type strawberry cultivar designated as 'Selva' which is the result of a cross between Cal 70.3-117 (not patented) and Cal 71.98-605 (not patented) made in 1975. The pedigree is as follows:

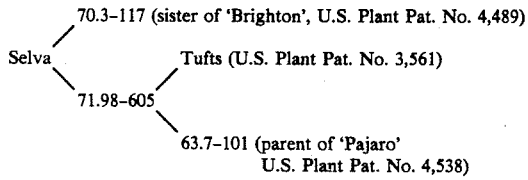

'Selva' first fruited at the University of California Wolfskill Experimental Orchards near Davis in 1976 where it was selected in 1977 and designated originally as Cal 75.71-107. It was tested later as advanced selection CN 18.

'Selva' has been propagated asexually by runners and has been tested at various University of California field stations and facilities and to a very limited extent in a few growers' fields under Test Agreement.

Figure 1:
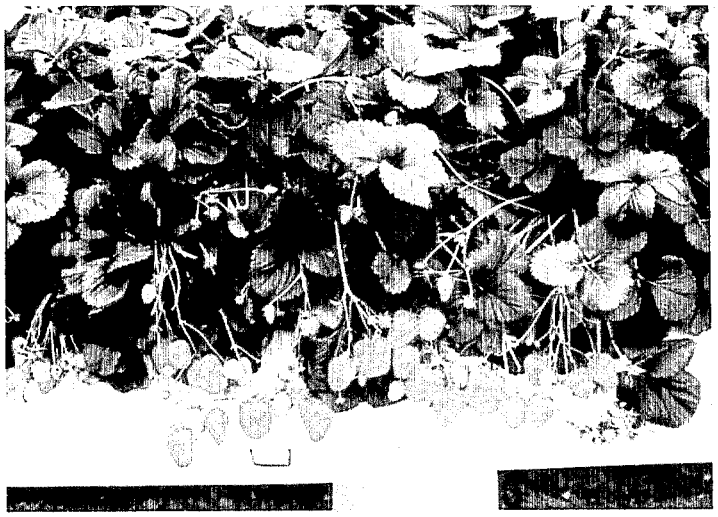
FIG. 1 shows typical growth, flowering and fruiting characteristics of the plant.
Figure 2:
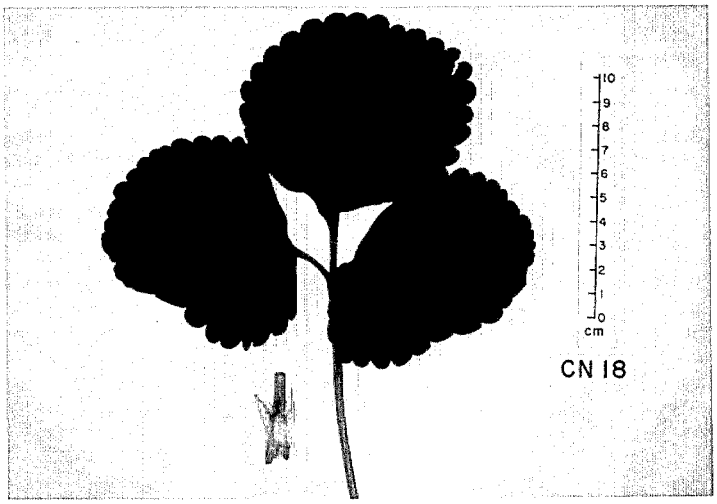
FIG. 2 shows a typical midsummer mature leaf from a plant in full fruit.
Figure 3:
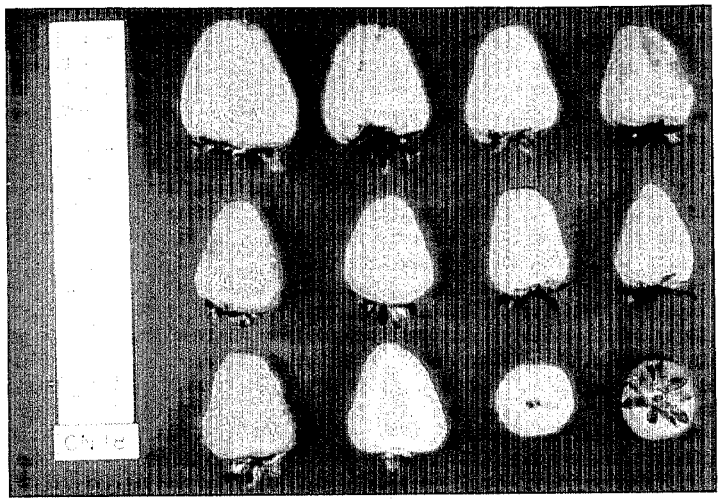
FIG. 3 shows representative early-season fruit with longitudinal and cross-sectional views.

'Selva' commences fruiting about three months after planting, whether fresh dug or cold storage plants are used, regardless of planting time provided that satisfactory growing conditions prevail. 'Selva' is not as strongly day-neutral as 'Aptos', Brighton' and 'Hecker'. The difference is most evident in the nursery where only the mother and first daughter plants of 'Selva' tend to flower and fruit strongly, whereas virtually all daughter plants of 'Aptos', 'Brighton' and 'Hecker' do so. 'Selva' is of interest for winter and summer plantings as well as at times when short-day plants will do nothing but runner if planted then.

PLANTS AND FOLIAGE

'Selva' plants are semi-erect in growth habit, larger than 'Hecker' and about the same size to slightly smaller than those of the standard 'Tioga' in both winter and summer plantings as estimated by measuring petiole length on plants in full fruit. Leaflets of 'Selva' are about the same size as those of 'Tioga' averaging about 2 serrations less per terminal half leaflet. Leaves are about the same color as those of 'Aiko', 7.5GY4/4 (Munsell Color System-Nickerson Color Fan) considerably less yellow than, but of about the same intensity as those of 'Tioga', 2.5GY4/3. Runner production in nursery plants is very good, comparable to or better than 'Hecker', but only the mother and first daughter plants flower and fruit in contrast to those of 'Hecker', all of which fruit. 'Selva' plants have a higher chilling requirement than 'Hecker' but will fruit in the winter under sufficiently warm growing conditions.

ISOZYMES IN LEAF EXTRACTS

'Selva' has been classified for three enzyme systems: (A) Phosphoglucoisomerase (PGI); (B) Leucine amino peptidase (LAP); and (C) Phosphoglucomutase (PGM) making it unique among the California cultivars (below):

| | 'Tioga' | 'Aptos' & 'Brighton' | 'Hecker' | 'Selva' |
|---|---|---|---|---|
| PGI | A1 | A4 | A1 | A2 |
| LAP | B1 | B3 | B1 | B3 |
| PGM | C3 | C4 | C4 | C2 |

*1981 J. Amer. Soc. Hort. Sci 106:684-687.

FLOWERING AND FRUITING

'Selva' is similar to California day-neutral cultivars 'Aptos', 'Brighton' and 'Hecker' in that with a minimum of conditioning, it will flower and fruit anytime, effectively independent of day length. Flowers are borne on long, relatively thick peduncles which remain semi-erect until the weight of the fruit brings them down. The flowers are self fertile with ample pollen through the season and consequently there is little malformed fruit.

FRUIT APPEARANCE

'Selva' fruit is medium to long conic with some flat and wedgy. Internally the fruit is somewhat hollow. The fruit skin color is about 7R4/11 (ibid), darker than that of fully colored 'Tioga' (about 7.5R4.5/13). The finish is bright and attractive. The flesh is about the same color with a somewhat lighter ring around the core. The achenes are bright yellow to reddish, positioned about flush with surface. The calyx is medium to large in size positioned from even with the base to being borne on a short neck and reflexed. The fruit is very firm and durable, firmer than that of 'Tioga', 'Tufts', 'Aiko' or 'Pajaro' according to penetrometer readings and handling comparisons. The fruit size averages much larger than that of 'Tioga' with a wide range in size as the season advances. There is almost always some exceptionally large fruit.

FRUIT QUALITY

'Selva' has averaged about as high ascorbic acid content as 'Tioga' (23 mg/100 g fresh fruit) as tested on summer and winter plantings during 1981 and 1982 by the method of Loeffler and Ponting (1942, J. Indust. and Engin. Chem. 14:846). Soluble solids readings for 'Selva' were not significantly different from those of 'Tioga', 'Tufts', 'Douglas', 'Aiko' or 'Pajaro' from comparable plantings. The flavor of 'Selva' is generally good, comparable to that of most of the cultivars now used in California in our opinion and according to most who have tried it. Some may object to the firmness and lower moisture content. It is suitable for fresh market and processing and for commercial usage as well as home gardening.

We claim:

1. The new and distinct variety of strawberry plant herein described and illustrated and identified by the characteristics enumerated above.

* * * * *